United States Patent
Hazama et al.

(10) Patent No.: US 7,366,626 B2
(45) Date of Patent: Apr. 29, 2008

(54) CALIBRATION METHOD AND ZIRCONIA-TYPE OXYGEN ANALYZER USING THIS METHOD

(75) Inventors: Kentaro Hazama, Musashino (JP); Makoto Ishii, Musashino (JP); Yukihiro Seki, Musashino (JP)

(73) Assignee: Yokogawa Electric Corporation, Musashino-shi (JP)

( * ) Notice: Subject to any disclaimer, the term of this patent is extended or adjusted under 35 U.S.C. 154(b) by 244 days.

(21) Appl. No.: 11/082,757

(22) Filed: Mar. 18, 2005

(65) Prior Publication Data

US 2005/0263408 A1 Dec. 1, 2005

(30) Foreign Application Priority Data

May 31, 2004 (JP) ............................. 2004-160570
Feb. 9, 2005 (JP) ............................. 2005-032847

(51) Int. Cl.
*G06F 19/00* (2006.01)

(52) U.S. Cl. ........................................ 702/104; 702/85

(58) Field of Classification Search ................ 204/424, 204/427; 73/1.03, 1.07, 1.06, 1.01, 1.02; 205/783.5, 784, 784.5, 785; 702/107, 85, 702/104, 31

See application file for complete search history.

(56) References Cited

U.S. PATENT DOCUMENTS

2004/0055359 A1* 3/2004 Ketler et al. ................ 73/1.07
2004/0139110 A1* 7/2004 LaMarca et al. ......... 707/104.1
2004/0260498 A1* 12/2004 Green et al. ................ 702/104

FOREIGN PATENT DOCUMENTS

JP          63238515 A   * 10/1988
JP          2005-338020  *  8/2005

* cited by examiner

*Primary Examiner*—John Barlow
*Assistant Examiner*—Douglas Washburn
(74) *Attorney, Agent, or Firm*—Westerman, Hattori, Daniels & Adrian, LLP.

(57) ABSTRACT

A calibration method in which secular change in sensor output values obtained at calibration times is estimated and the next calibration date can be determined at an appropriate interval and a zirconia-type oxygen analyzer using the above calibration method is achieved. The present invention is characterized by the fact that, in a calibration method in which a standard sample having a known value is measured and the output value of a measuring instrument corresponding to a sensor output value at the time of measurement is calibrated, the sensor output value obtained in implemented calibrating operations is stored in succession as the data for calibration history and the state of secular change in said sensor output value is estimated based on the stored past data for calibration history to determine the next calibration date.

15 Claims, 5 Drawing Sheets

Data for calibration history

| Data ID | Calibration date | Sensor EMF |
|---------|------------------|------------|
| P1      | 2004.01.01       | e1         |
| P2      | 2004.02.01       | e2         |
| P3      | 2004.03.01       | e3         |

CALIBRATION METHOD AND ZIRCONIA-TYPE OXYGEN ANALYZER USING THIS METHOD

BACKGROUND OF THE INVENTION

1. Field of the Invention

The present invention relates to a calibration method suitable for application to measuring instruments accompanied by secular change in sensor output values such as zirconia-type oxygen analyzers.

2. Description of the Prior Art

FIG. 1 shows a cross-sectional view indicating the measurement principle of a zirconia-type sensor which is an example of sensors whose outputs vary (decrease) with time. In FIG. 1, sensor 1 is composed of zirconia tube 100 and electrodes 101 and 102 provided on the outer periphery and inner periphery thereof, and generally, porous platinum electrodes are used for electrodes 101 and 102. In zirconia-type sensor 1 having configured as described above, if a reference gas is passed along the outside of zirconia tube 100 (flow path of the reference gas) and a gas to be measured is passed along the inside of zirconia tube 100 (flow path of the gas to be measured) after heating the zirconia tube up to a high temperature of about 750° C., an EMF Vout corresponding to the difference of oxygen concentrations between the reference gas and the gas to be measured is generated between electrodes 101 and 102. The EMF Vout is proportional to the logarithm of the ratio of the oxygen concentrations, and the oxygen concentration of a gas to be measured can be determined from the value of the EMF Vout by using a gas whose oxygen concentration is known, such as air, as the reference gas.

FIG. 2 is a configuration drawing showing an example of conventional zirconia-type oxygen analyzers, which uses zirconia-type sensor 1. In FIG. 2, numeral 1 denotes a zirconia-type sensor as shown in the above indicated FIG. 1, numeral 2 denotes a converter which receives an EMF generated at zirconia-type sensor 1 and converts the EMF to a measured output signal corresponding to the oxygen concentration of a gas to be measured, numeral 3 a heater for heating up zirconia-type sensor 1, numeral 4 the heater power line supplying electric power to heater 3, numeral 5 the temperature control signal line for controlling the temperature of heater 3, numeral 6 the sensor output signal line, and numeral 7 the converter output signal line to transmit the measured output signal obtained by converter 2. Converter 2 also includes a temperature control system, not shown in the drawing, for holding the temperature of zirconia-type sensor 1 to a prescribed temperature.

Further, numeral 8 denotes a standard gas called "span gas" and numeral 9 denotes another standard gas called "zero gas," and both standard gases are enclosed in each gas cylinder respectively. In general, "span gas" 8 is a gas containing 21% oxygen and 79% nitrogen, and "zero gas" 9 is a gas containing 1% oxygen and 99% nitrogen, and air is used for "span gas" 8. Numerals 10 to 13 denote control valves for switching the flow paths of gases which are supplied to zirconia-type sensor 1. Each operation of control valves 10 to 13 is controlled by converter 2.

In a zirconia-type oxygen analyzer configured as described above, at the time of measuring operations, "span gas" 8 is supplied to the flow path of the reference gas in zirconia-type sensor 1 through control valve 10, and at the same time, a sampled gas (gas supplied for the purpose of measurement) is selected by control valve 13 and supplied to the flow path of the gas to be measured in zirconia-type sensor 1 through control valve 11. As a result, an EMF corresponding to the difference of oxygen concentrations between the gas to be measured (sampled gas) and the reference gas ("span gas" 8) is generated from zirconia-type sensor 1. This EMF is converted to a converter output signal (4 to 20 mA) corresponding to an oxygen concentration of the gas to be measured (sampled gas) with converter 2 and the signal is transmitted via converter output signal line 7.

Next, at the time of calibrating operation, "span gas" 8 is supplied to the flow path of the reference gas in zirconia-type sensor 1 through control valve 10, and at the same time, control valve 13 is changed over to the calibration gas port and "span gas" 8 or "zero gas" 9 is selectively supplied to the flow path of the gas to be measured through control valves 11 to 13. That is, by changing over control valve 12 to "span gas" 8 port, "span gas" 8 is passed through the flow path of the gas to be measured of zirconia-type sensor 1 and thus calibration of converter 2 (span calibration) is performed for a sensor output corresponding to the oxygen concentration of "span gas" 8. Also, calibration of converter 2 (zero calibration) is performed for a sensor output corresponding to the oxygen concentration of "zero gas" 9 by changing over control valve 12 to "zero gas" 9 port to pass "zero gas" 9 through the flow path of the gas to be measured in zirconia-type sensor 1.

(Patent Document 1)

Gazette for Japanese Laid-open Patent Application No. 2000-266719

Although the above mentioned calibrating operation is performed to output correct oxygen concentrations removing the influence of sensor deterioration and the like, clear standards are not shown for the timing to carry out calibrating operations and so in the current situation, it is up to the users to implement calibration periodically based on the user's experience.

For this reason, if the interval between calibrations is too long, the accuracy of measurements deteriorates and vice versa, if the interval is too short, calibrating operations take time and thus the working life of the measuring instrument is shortened. In addition, "zero gas" 9 is more expensive than "span gas" 8 which has the same constituents as air because the oxygen concentration of "zero gas" 9 is adjusted to a required value, and thus the more the number of calibrating operations increases, the more expensive standard gases are consumed.

The present invention aims at achieving a calibration method which removes the disadvantages in the above described conventional method, estimates the secular change of the sensor from the sensor output values at each calibration, and can determine the next appropriate calibration date, and also achieve zirconia-type oxygen analyzers using this method.

SUMMARY OF THE INVENTION

In order to achieve the above mentioned purposes, claim 1 of the present invention is characterized by the following: A calibration method in which a standard sample having a known value is measured and an output value of a measuring instrument is calibrated corresponding to a sensor output value at the time of this measurement, further storing the above sensor outputs in succession as the data for calibration history, and estimating the state of secular change in output values of the above sensor based on the stored past data for calibration history, to determine the next calibration date.

Claim 2 of the present invention is characterized by the fact that, in the calibration method mentioned in claim 1, secular change in output values in the above sensor output value is estimated using regression analysis based on the above data for calibration history.

Claim 3 of the present invention is characterized by the fact that, in the calibration method mentioned in claim 1 or claim 2, estimation of secular change in output values in the above sensor is performed based on the data for calibration history obtained at three or more calibration points in time and if the number of calibration points in time where the data for calibration history are taken and stored is less than three, the next calibration date is determined at a prescribed interval.

Claim 4 of the present invention is characterized by the fact that, in the calibration method mentioned in claim 3, calibrating operations are caused to be carried out on the appropriate day based on the next calibration date determined above.

Claim 5 of the present invention is characterized by the fact that the calibration method mentioned in claim 3 has a function to reset the above stored data for calibration history.

Claim 6 of the present invention is characterized by the fact that in the calibration method in claim 3, a calibration coefficient determined from the sensor output value provided at the time of calibration operations is stored as the data for calibration history and sensor output values used for estimating the state of secular change in output values of the above sensor are calculated according to the calibration coefficient.

Claim 7 of the present invention is characterized by the fact that a zirconia-type oxygen analyzer which contains a zirconia-type sensor and generates an EMF corresponding to each difference in oxygen concentration between a gas to be measured and a reference gas, calibrates the converter output by supplying a standard gas whose oxygen concentration is known to the flow path of the gas to be measured in the above sensor when performing calibration, and stores this sensor EMF in succession as the data for calibration history, estimates the state of secular change in the above sensor EMF based on the stored past data for calibration history, then determines the next calibration date.

Claim 8 of the present invention is characterized by the fact that, in the zirconia-type oxygen analyzer mentioned in claim 7, zero calibration and span calibration are performed using "zero gas" and "span gas" as the above described standard gases and a sensor EMF corresponding to a calibration point where the sensor EMF is larger is stored as the data for calibration history at that time.

Claim 9 of the present invention is characterized by the fact that, in a zirconia-type oxygen analyzer mentioned in claim 7 or claim 8, secular change in the above sensor EMF is estimated using regression analysis based on the above data for calibration history.

Claim 10 of the present invention is characterized by the fact that, in the zirconia-type oxygen analyzer mentioned in claim 9, the estimation of secular change in the above sensor EMF is performed based on the data for calibration history obtained at three or more calibration points in time and if the number of points where the data for calibration history were stored is less than three, the next calibration date is determined at a prescribed interval.

Claim 11 of the present invention is characterized by the fact that, in the zirconia-type oxygen analyzer mentioned in claim 10, calibrating operations are caused to be carried out on the appropriate day based on the above determined next calibration date.

Claim 12 of the present invention is characterized by the fact that the zirconia-type oxygen analyzer mentioned in claim 10 is provided with a means to reset the above stored data for calibration history.

Claim 13 of the present invention is characterized by the fact that the zirconia-type oxygen analyzer mentioned in claim 10 stores coefficients for an equation used to determine oxygen concentrations from the sensor EMF provided at the time of calibration operations as the data for calibration history, and calculates sensor EMFs used for estimating the state of secular change in the above sensor EMF.

As described above, operations in which the sensor output value is stored in succession in each calibrating operation and the next calibration date is determined by estimation of secular change states in sensor output values based on the stored past data for calibration history, enable the sensor-specific secular change to be grasped, and the number of calibrations can be kept to the minimum within the range in which the accuracy of that measuring instrument is guaranteed.

In addition, if this calibration method is applied to zirconia-type oxygen analyzers, calibrating operations can be performed at an appropriate timing and excess consumption of expensive standard gases can be eliminated.

Furthermore, as described above, a calibration coefficient determined from the sensor output value provided at the time of calibration operations is stored as the data for calibration history, and sensor output values at the time of subsequent calibration operations are calculated according to the calibration coefficient. As a result, even if the sensor output value varies for reasons other than secular changes in the sensor, it is possible to determine a sensor output value corrected against the amount of such variation. Thus, the past data for calibration history can be effectively utilized to predict the state of secular changes in the output value of the sensor.

DESCRIPTION OF THE PREFERRED EMBODIMENT

The calibration method of the present invention and a zirconia-type oxygen analyzer using the method are described below using drawings.

Figure 3:
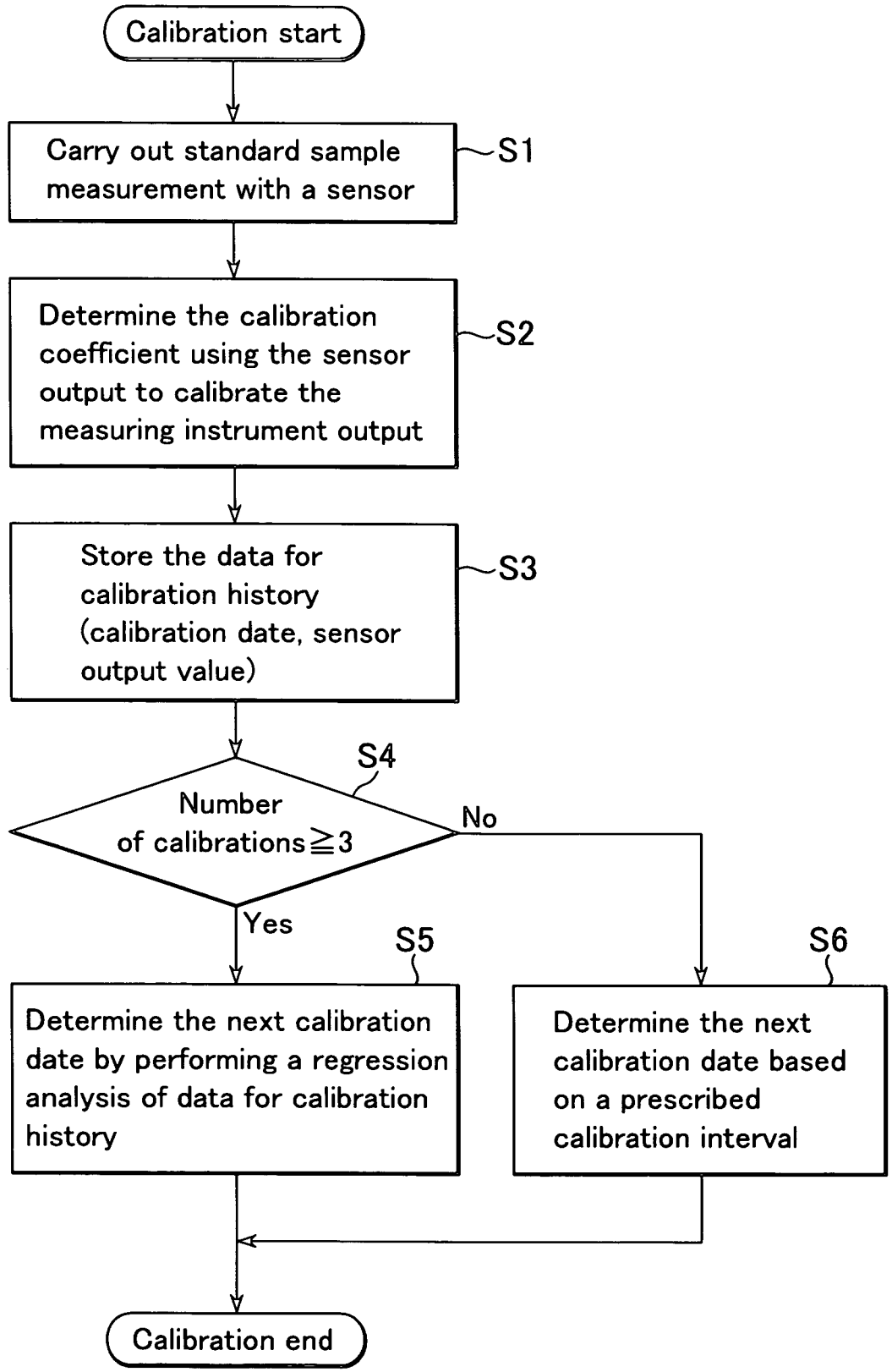
FIG. 3 is a flow diagram indicating an embodiment of the calibration method of the present invention.

FIG. 3 is a flow diagram indicating an embodiment of the calibration method of the present invention. As shown in the diagram, in the calibration method of the present invention, a standard sample having a known value is first measured by the sensor (S1). Next, the calibration coefficient is calculated so that the indicated value of the measuring instrument shows the predetermined value (value of standard sample) for the sensor output value at that time to calibrate the measuring instrument output (S2).

In addition, the sensor output value at that time is also stored as the data for calibration history together with the calibration date (S3).

Next, the number of calibration points in time is detected (S4) and if the above number of calibrations is equal to or larger than three, these data for calibration history for calibrations at each point are subjected to regression analysis to estimate the state of secular change in sensor outputs.

Further, from the result of this regression analysis the next calibration date is determined as the date on which the sensor output value will exceed the prescribed range (S5).

While, if the stored number of calibrations is less than three, the next calibration date is determined based on the prescribed calibration interval because the state of secular change in the sensor output cannot be accurately estimated by regression analysis (S6).

Furthermore, other than the above calibrating operations, if the data for calibration history stored so far becomes meaningless because of sensor maintenance and the like, data already stored for calibration history are reset to start storage of data for calibration history again.

As described above, causing estimation of the state of secular change in sensor output values based on the past data for calibration history enables the next appropriate calibration date to be set for every series of calibrating operations and thus the number of calibrations can be kept to the minimum within the range in which the accuracy of the measuring instrument is guaranteed.

Figure 1:
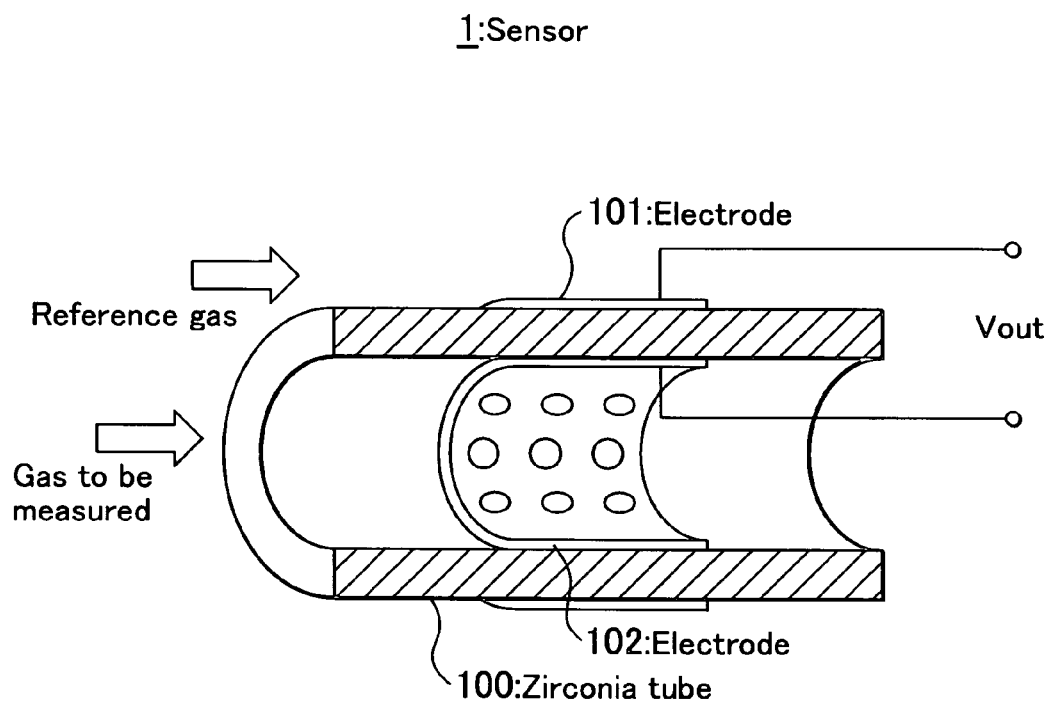
FIG. 1 is a cross sectional drawing indicating the measuring principle of a zirconia-type sensor.
Figure 2:
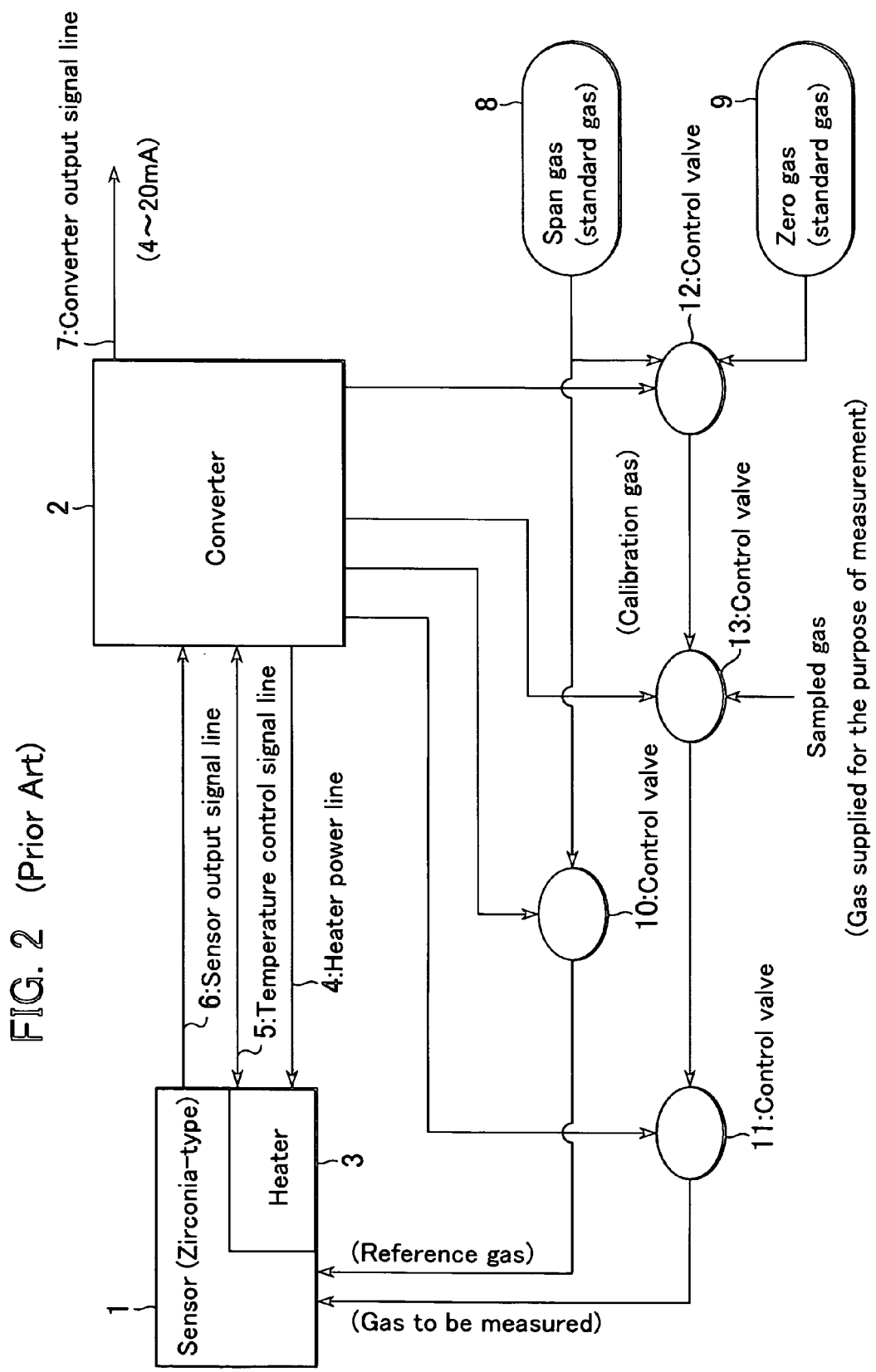
FIG. 2 is a configuration drawing indicating an example of conventional oxygen analyzers using a zirconia-type sensor.
Figure 4:
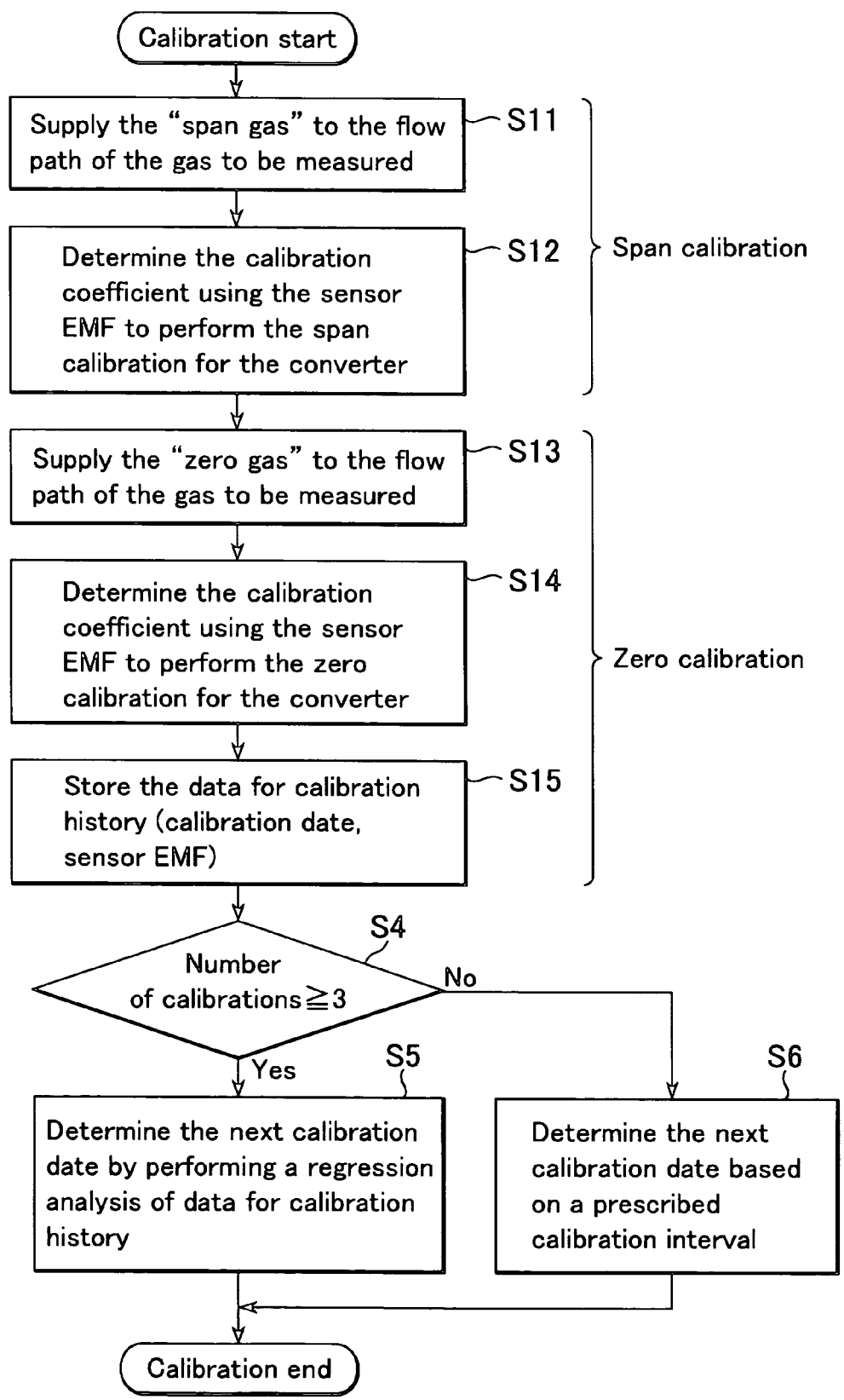
FIG. 4 is a flow diagram indicating an embodiment of the calibration method of the present invention applied to a zirconia-type oxygen analyzer as shown in FIG. 2.

FIG. 4 is a flow diagram indicating an embodiment of the calibration method of the present invention applied to a zirconia-type oxygen analyzer as shown in the above FIG. 2. In FIG. 4, items same as those shown in FIG. 3 are shown with the same signs as those in FIG. 3. In calibrating operations in a zirconia-type oxygen analyzer as shown in FIG. 2, "span gas" 8 is supplied to the reference gas flow path of zirconia-type sensor 1 through control valve 10 and at the same time control valve 13 is changed over to the calibration gas port and control valve 12 is changed over to the span gas port, and "span gas" 8 is supplied to the flow path of the gas to be measured in zirconia-type sensor 1 through control valves 11 to 13 (S11).

In this state, span calibration is performed (S12). That is, since "span gas" 8 flows through the flow path of the gas to be measured in zirconia-type sensor 1, the calibration coefficient for bringing the output of converter 2 to a value corresponding to the oxygen concentration of "span gas" 8 is determined and so the output of converter 2 is subjected to span calibration. In addition, since oxygen concentration of the gas flowing through the reference gas flow path becomes equal to oxygen concentration of the gas flowing through the flow path of the gas to be measured in zirconia-type sensor 1, the sensor EMF in this case is ideally zero.

Next, control valve 12 is changed over to the zero gas port, and "zero gas" 9 is supplied to the flow path of the gas to be measured in zirconia-type sensor 1 through control valves 11 to 13 (S13).

In this state, zero calibration is carried out (S14). That is, since "zero gas" 9 is passed through the flow path of the gas to be measured in zirconia-type sensor 1, the calibration coefficient for bringing the output of converter 2 to a value corresponding to the oxygen concentration of "zero gas" 9 is determined and so the output of converter 2 is subjected to zero calibration. In this case, the sensor EMF shows a value corresponding to the difference in oxygen concentrations between "span gas" 8 and "zero gas" 9.

Further, this sensor EMF is stored as the data for calibration history (S15). Although, in a series of calibrating operations, two calibration data (sensor EMFS) are obtained at span calibration and zero calibration, the data at zero calibration are stored as the data for calibration history because the sensor EMF itself at the zero calibration is larger than that obtained at the span calibration.

Figures 5, 6:
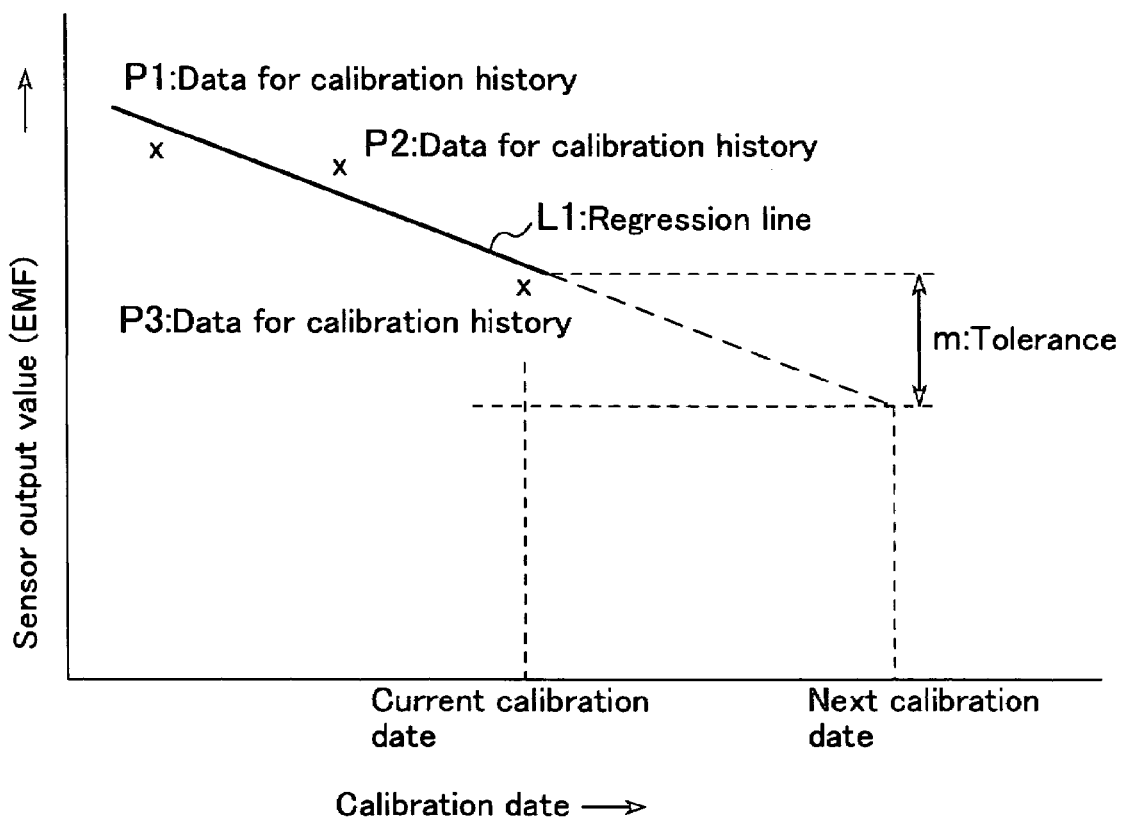
FIG. 5 is a diagram indicating the form of stored data for the data for calibration history.
FIG. 6 is a graph indicating an example of regression analysis for the data P1 to P3 for calibration history at three calibration points in time.

FIG. 5 is a diagram indicating the form of stored data for the data for calibration history. As shown in FIG. 5, one data group is composed of each element of data ID, calibration date, and sensor EMF and, in this case, three groups of data, P1 to P3, are stored. For example, in data group P1, the calibration date is 2004, 01, 01 (Jan. 1, 2004) and the sensor EMF at that time is "e1".

FIG. 6 is a graph indicating the regression analysis for the data groups for calibration history P1 to P3. In FIG. 6, L1 shows the regression line obtained by regression analysis, and this line is calculated using the least squares method.

After regression line L1 is obtained, the day on which the changed amount of sensor EMF reaches tolerance m is calculated from this line and this day is determined as the next calibration day (S5).

In this case, tolerance m is determined in accordance with the guaranteed accuracy of the zirconia-type oxygen analyzer used. For example, if it is assumed that an accuracy of 0.5% against the full scale is guaranteed, accuracy can be maintained within 0.5% if the changed amount of sensor EMF lies in tolerance m using sensor EMF (e3) as a reference when calibration is performed.

Accordingly, by calculating the day on which the changed amount of sensor EMF reaches tolerance m and determining the day as the next calibration day, the number of calibrations can be kept to the minimum within the range in which the accuracy of that zirconia-type oxygen analyzer is guaranteed.

In addition, excessive consumption of the expensive standard gas ("zero gas" 9) is eliminated by keeping the number of calibrations to the minimum.

Further, although data for calibration history for three or more points are used to perform more accurate regression analysis in the above description, if the number of data groups for calibration history does not reach three (that is, is less than three), the next calibration date is determined based on a calibration interval predetermined as suitable for the analyzer system such as, for example, ten days or one month (S6).

In the above description, an example of carrying out calibration in the order of span calibration and then zero calibration in a series of calibrating operations is shown. However, the sequence of calibration is not limited to this example and thus calibration may also be carried out in the order of zero calibration and then span calibration.

Also, in the above description, although an example of determining the next calibration date by estimating the state of secular change in the sensor output value based on the stored past data for calibration history, calibrating operations can be automatically carried out on a day appropriate to the next calibration date, not limited to determination of the next calibration date.

In other words, if a measuring instrument is configured to start up a sequence for calibrating operations automatically on the next calibration date by using the scheduling function of the instrument, a measuring instrument which repeats calibrating operations at appropriate intervals can be achieved.

The next calibration date can also be specified by using the hours and minutes, not only the date.

In addition, in the above embodiments, although an example in which the data for calibration history are stored in succession for every implementation of calibrating operations is shown, if zirconia-type sensor 1 is replaced, the data for calibration history accumulated so far become entirely meaningless. Therefore, in such cases, storing the data for calibration history is started again after resetting the stored data for calibration history.

That is, after the data for calibration history are reset, the next calibration date is determined based on a prescribed calibration interval because the number of stored data group for calibration history is less than three.

In the description provided above, an example has been given in which sensor EMF (sensor output values) is stored in succession as data for calibration history and the state of secular changes in the sensor EMF is predicted according to the calibration history data. Alternatively, as the data to be stored for calibration history, it is possible to store coefficients (calibration coefficients) for an equation (Nernst equation) used to determine oxygen concentrations from the sensor EMF.

The calibration coefficients are thus stored together with the sensor EMF or in place thereof, and, when predicting the state of secular changes in the sensor EMF, the magnitude of the sensor EMF at the time of each calibration operation equivalent to a desired oxygen concentration is calculated according to the stored calibration coefficients.

The reason for this is that possible causes for changes in the sensor EMF include changes in the oxygen concentration of a calibration gas in addition to secular changes in the sensor. If the oxygen concentration of the calibration gas changes due to an exchange of the gas, for example, the sensor EMF also changes. As a result, it is no longer possible to make reference to the values of the sensor EMF that have been stored to date In that regard, the calibration method described above is advantageous since the magnitude of the sensor EMF at the time of each calibration operation can be calculated by specifying a desired oxygen concentration, only if calibration coefficients are stored as the data for calibration history, as described above. Thus, even if the oxygen concentration of the calibration gas changes, the past data for calibration history can be effectively utilized to predict the state of secular changes in the output value of the sensor.

Accordingly, there is no need for resetting the data for calibration history even if the oxygen concentration of the calibration gas changes and the next calibration date can be determined at the appropriate point in time.

What is claimed is:

1. A calibration method in which a standard sample having a known value is measured and an output value of a measuring instrument is calibrated corresponding to a sensor output value at the time of this measurement, comprising:
    storing said sensor output value in succession as the data for calibration history, and
    estimating the state of secular change in said sensor output value based on the stored past data for calibration history and determining the next calibration date based on the estimated state of secular change at the time when the current calibration has completed.

2. A calibration method in accordance with claim 1, wherein secular change in said sensor output value is estimated using regression analysis based on said data for calibration history.

3. A calibration method in which a standard sample having a known value is measured and an output value of a measuring instrument is calibrated corresponding to a sensor output value at the time of this measurement, comprising:
    storing said sensor output value in succession as the data for calibration history, and
    estimating the state of secular change in said sensor output value based on the stored past data for calibration history, and determining the next calibration date based on the estimated state of secular change,
    wherein estimation of secular change in output values of said sensor is performed based on the data for calibration history obtained at three or more points of calibration in time and if the number of points of calibration in time is less than three, the next calibration date is determined based on a prescribed interval.

4. A calibration method in accordance with claim 3, wherein secular change in said sensor output value is estimated using regression analysis based on said data for calibration history.

5. A calibration method in accordance with claim 3 or claim 4, wherein calibrating operations are caused to be carried out on the appropriate day based on the next calibration date determined in said manner.

6. A calibration method in accordance with claim 3 or claim 4, which has a function for resetting said stored data for calibration history.

7. A calibration method in accordance with claim 3 or claim 4, wherein a calibration coefficient determined from said sensor output value provided at the time of calibration operations is stored as said data for calibration history and sensor output values used for estimating the state of secular change in output values of the above sensor are calculated according to the calibration coefficient.

8. A zirconia-type oxygen analyzer which contains a zirconia-type sensor and generates an electromotive force (EMF) corresponding to each difference in oxygen concentration between a gas to be measured and a reference gas, and when calibrating operations are carried out, calibrates the converter output by supplying a standard gas whose oxygen concentration is known to the flow path of the gas to be measured in said sensor as well as stores the sensor electromotive force (EMF) at that time as the data for calibration history in succession, estimates the state of secular change in said sensor electromotive force (EMF) based on the stored past data for calibration history, then determines the next calibration date.

9. A zirconia-type oxygen analyzer in accordance with claim 8, wherein zero calibration and span calibration are performed using "zero gas" and "span gas" as said standard gases and a sensor electromotive force (EMF) corresponding to a calibration point where the sensor electromotive force (EMF) is larger is stored as the data for calibration history at that time.

10. A zirconia-type oxygen analyzer in accordance with claim 8 or claim 9, wherein secular change in said sensor electromotive force (EMF) is estimated using regression analysis based on said data for calibration history.

11. A zirconia-type oxygen analyzer which contains a zirconia-type sensor and generates an electromotive force (EMF) corresponding to each difference in oxygen concentration between a gas to be measured and a reference gas, and when calibrating operations are carried out, calibrates the converter output by supplying a standard gas whose oxygen concentration is known to the flow path of the gas to be measured in said sensor as well as stores the sensor electromotive force (EMF) at that time as the data for calibration history in succession, estimates the state of secular change in said sensor electromotive force (EMF) based on the stored past data for calibration history, then determines the next calibration date, wherein secular change in said sensor electromotive force (EMF) is estimated using regression analysis based on said data for calibration history, and wherein estimation of secular change in output values of said sensor is performed based on the data for calibration history obtained at three or more points of calibration in time and if the number of points of calibration in time is less than three, the next calibration date is determined based on a prescribed interval.

12. A zirconia-type oxygen analyzer in accordance with claim 11, wherein zero calibration and span calibration are performed using "zero gas" and "span gas" as said standard gases and a sensor electromotive force (EMF) corresponding to a calibration point where the sensor electromotive force (EMF) is larger is stored as the data for calibration history at that time.

13. A zirconia-type oxygen analyzer in accordance with claim 11 or claim 12, wherein calibrating operations are caused to be carried out on the appropriate day based on the next calibration date determined in said manner.

14. A zirconia-type oxygen analyzer in accordance with claim 11 or claim 12, which is provided with a means for resetting said stored data for calibration history.

15. A zirconia-type oxygen analyzer in accordance with claim 11 or claim 12, wherein said zirconia-type oxygen analyzer stores coefficients for an equation used to determine oxygen concentrations from said sensor electromotive force (EMF) provided at the time of calibration operations as said data for calibration history, and calculates sensor electromotive force (EMF) used for estimating the state of secular change in the above sensor electromotive force (EMF).

\* \* \* \* \*